(12) United States Patent
Niedermeyer (10) Patent No.: US 10,201,571 B2
(45) Date of Patent: *Feb. 12, 2019

(54) NANOPARTICLE COMPOSITIONS AND METHODS FOR TREATING ONYCHOMYCOSIS

(71) Applicant: ATTOSTAT, INC., Salt Lake City, UT (US)

(72) Inventor: William H. Niedermeyer, West Jordan, UT (US)

(73) Assignee: ATTOSTAT, INC., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/415,562

(22) Filed: Jan. 25, 2017

(65) Prior Publication Data
US 2017/0209490 A1   Jul. 27, 2017

Related U.S. Application Data

(60) Provisional application No. 62/286,768, filed on Jan. 25, 2016.

(51) Int. Cl.
| A61K 33/38 | (2006.01) |
| A61K 33/24 | (2006.01) |
| A61K 47/20 | (2006.01) |
| A61K 47/12 | (2006.01) |
| A61K 9/14 | (2006.01) |
| A61K 9/06 | (2006.01) |
| A61K 9/00 | (2006.01) |

(52) U.S. Cl.
CPC ............ *A61K 33/38* (2013.01); *A61K 9/0014* (2013.01); *A61K 9/06* (2013.01); *A61K 9/14* (2013.01); *A61K 33/24* (2013.01); *A61K 47/12* (2013.01); *A61K 47/20* (2013.01); *Y10S 977/773* (2013.01); *Y10S 977/775* (2013.01); *Y10S 977/777* (2013.01)

(58) Field of Classification Search
None
See application file for complete search history.

(56) References Cited

U.S. PATENT DOCUMENTS

| 3,133,023 A | 5/1964 | Vogel |
| 4,515,740 A | 5/1985 | Schuttenberg et al. |
| 5,047,448 A | 9/1991 | Tanaka |
| 5,227,608 A | 7/1993 | Yoshida |
| 5,390,864 A | 2/1995 | Alexander |
| 5,585,020 A | 12/1996 | Becker et al. |
| 6,232,264 B1 | 5/2001 | Lukehart |
| 6,239,453 B1 | 5/2001 | Yamada et al. |
| 6,509,070 B1 | 1/2003 | Voevodin et al. |
| 7,014,737 B2 | 3/2006 | Harutyunyan et al. |
| 7,332,351 B2 | 2/2008 | Tan |
| 7,371,457 B2 | 5/2008 | Oldenburg et al. |
| 7,374,730 B2 | 5/2008 | Simard et al. |
| 7,384,560 B2 | 6/2008 | Martens et al. |
| 7,449,679 B2 | 11/2008 | Plewa |
| 7,509,993 B1 | 3/2009 | Turng et al. |
| 7,527,824 B2 | 3/2009 | Becker |
| 7,553,801 B2 | 6/2009 | Alexander et al. |
| 7,625,637 B2 | 12/2009 | Kim |
| 7,662,731 B2 | 2/2010 | Itoh et al. |
| 7,682,970 B2 | 3/2010 | Grigoropoulos et al. |
| 7,700,032 B1 | 4/2010 | Lu et al. |
| 7,884,160 B2 | 2/2011 | Wang et al. |
| 7,967,876 B2 | 6/2011 | Aradi |
| 7,985,367 B2 | 7/2011 | Hiromatsu et al. |
| 8,097,233 B2 | 1/2012 | Porterat |
| 8,435,602 B1 | 5/2013 | Seal |
| 8,490,586 B2 | 7/2013 | Gardenier |
| 8,524,139 B2 | 9/2013 | Toth |
| 8,685,293 B1 | 4/2014 | Coppa et al. |
| 8,883,865 B2 | 11/2014 | DiFrancesco |
| 8,992,815 B2 | 3/2015 | Hu |
| 9,434,006 B2 * | 9/2016 | Niedermeyer ............ B22F 9/04 |

(Continued)

FOREIGN PATENT DOCUMENTS

| CN | 102120619 | 7/2011 |
| CN | 103891558 | 7/2014 |

(Continued)

OTHER PUBLICATIONS

Mycozil. "The Benefits of Colloidal Silver for Toenail Fungus." http://www.nailfungustoenail.com/benefitsofcolloidalsilverfortoenailfungus.html, downloaded by examiner on Mar. 14, 2017, published on Sep. 5, 2012, 3 printed pages.*

PG Hultin. "A Guide to Solvents and Reagents in Introductory Organic Chemistry for students in 2.222." Obtained from https://home.cc.umanitoba.ca/~hultin/chem2220/Support/solvents_and_reagents.pdf on Jan. 25, 2018. Originally published Feb. 12, 2002, 17 printed pages. (Year: 2002).*

Badawy et al., "Surface Charge-Dependent Toxicity of Silver Nanoparticles", Environ. Sci. Technol. 2011, 45, 283-287.

(Continued)

*Primary Examiner* — Isaac Shomer
(74) *Attorney, Agent, or Firm* — Workman Nydegger (57) ABSTRACT

A nanoparticle composition for treating onychomycosis includes spherical-shaped nanoparticles having a particle size and a particle size distribution and coral-shaped nanoparticles having a particle size and a particle size distribution mixed within a penetrating solvent configured to deliver the nanoparticles to target area of a nail and/or surrounding tissue. The nanoparticle composition can be mixed with a carrier to provide or augment application of the nanoparticle composition to a target area. The penetrating solvent can deliver the nanoparticles to an infected area within the nail and/or at the bed of the nail so as to kill or deactivate the fungal microbes causing the onychomycosis.

20 Claims, 9 Drawing Sheets

(56) References Cited

U.S. PATENT DOCUMENTS

| | | | |
|---|---|---|---|
| 9,839,652 B2* | 12/2017 | Tarbet | A61K 33/38 |
| 9,885,001 B2* | 2/2018 | Niedermeyer | C10L 1/1208 |
| 2001/0031564 A1 | 10/2001 | Suzuki et al. | |
| 2002/0051823 A1 | 5/2002 | Yan | |
| 2003/0086859 A1 | 5/2003 | Kawakami et al. | |
| 2003/0102099 A1 | 6/2003 | Yadav et al. | |
| 2004/0214001 A1 | 10/2004 | Oldenburg et al. | |
| 2005/0061785 A1 | 3/2005 | Schroder | |
| 2005/0153071 A1 | 7/2005 | Bouvrette | |
| 2005/0247866 A1 | 11/2005 | Plewa | |
| 2005/0258149 A1 | 11/2005 | Glukhoy | |
| 2005/0260276 A1* | 11/2005 | Yang | A61K 9/1075 424/492 |
| 2006/0049034 A1 | 3/2006 | Lee | |
| 2006/0142853 A1 | 6/2006 | Wang et al. | |
| 2007/0003603 A1 | 1/2007 | Karandikar | |
| 2007/0029185 A1 | 2/2007 | Tung | |
| 2007/0140951 A1 | 6/2007 | O'Brien | |
| 2007/0207335 A1 | 9/2007 | Karandikar | |
| 2007/0269576 A1* | 11/2007 | Barton | A23L 2/02 426/599 |
| 2007/0287202 A1 | 12/2007 | Maehashi et al. | |
| 2008/0006524 A1 | 1/2008 | Liu | |
| 2008/0035682 A1 | 2/2008 | Coffey et al. | |
| 2008/0044148 A1 | 2/2008 | Robinson | |
| 2008/0050448 A1 | 2/2008 | Wilson et al. | |
| 2008/0143021 A1 | 6/2008 | Ehrentraut | |
| 2008/0161631 A1 | 7/2008 | Axtell et al. | |
| 2008/0263940 A1 | 10/2008 | Parish et al. | |
| 2008/0292673 A1 | 11/2008 | Crudden | |
| 2009/0000186 A1 | 1/2009 | Sanders et al. | |
| 2009/0028947 A1 | 1/2009 | Rahman | |
| 2009/0061230 A1 | 3/2009 | Berkei | |
| 2009/0104179 A1 | 4/2009 | Boyden | |
| 2009/0148484 A1 | 6/2009 | Lin et al. | |
| 2009/0191288 A1 | 7/2009 | Squires | |
| 2009/0246530 A1 | 10/2009 | Murakami et al. | |
| 2010/0040655 A1 | 2/2010 | Ren et al. | |
| 2010/0050872 A1 | 3/2010 | Lee | |
| 2010/0068299 A1 | 3/2010 | van der Krieken et al. | |
| 2010/0072645 A1 | 3/2010 | Hiromatsu et al. | |
| 2010/0080957 A1 | 4/2010 | Chinn | |
| 2010/0092367 A1 | 4/2010 | Porterat | |
| 2010/0154591 A1* | 6/2010 | Islam | B22F 1/0018 75/345 |
| 2010/0167958 A1 | 7/2010 | Lin | |
| 2010/0172997 A1 | 7/2010 | Omary | |
| 2010/0180413 A1 | 7/2010 | Jeong | |
| 2010/0183739 A1 | 7/2010 | Newman | |
| 2010/0187091 A1 | 7/2010 | Pierce et al. | |
| 2010/0196192 A1 | 8/2010 | Liu et al. | |
| 2010/0212221 A1 | 8/2010 | Aradi | |
| 2010/0255110 A1 | 10/2010 | Yoon | |
| 2010/0272650 A1 | 10/2010 | Tsukada | |
| 2010/0301013 A1 | 12/2010 | Conneely | |
| 2011/0039078 A1 | 2/2011 | Brennan Fournet et al. | |
| 2011/0052460 A1 | 3/2011 | Coffey et al. | |
| 2011/0155643 A1 | 6/2011 | Tov | |
| 2011/0192450 A1 | 8/2011 | Liu | |
| 2011/0193025 A1 | 8/2011 | Ichikawa et al. | |
| 2011/0196044 A1 | 8/2011 | Hu | |
| 2011/0201527 A1 | 8/2011 | Lin | |
| 2011/0228890 A1 | 9/2011 | Dean et al. | |
| 2011/0244056 A1 | 10/2011 | Santra | |
| 2011/0297653 A1 | 12/2011 | Ehrentraut | |
| 2012/0088066 A1 | 4/2012 | Aytug et al. | |
| 2012/0124899 A1 | 5/2012 | Difrancesco | |
| 2012/0136164 A1 | 5/2012 | Ying et al. | |
| 2012/0138862 A1 | 6/2012 | Hogan | |
| 2012/0164073 A1 | 6/2012 | Xu et al. | |
| 2012/0174472 A1 | 7/2012 | Mills | |
| 2012/0183674 A1 | 7/2012 | Bonn-Savage | |
| 2012/0301528 A1 | 11/2012 | Uhlmann | |
| 2012/0301531 A1 | 11/2012 | Uhlmann et al. | |
| 2013/0001833 A1* | 1/2013 | Niedermeyer | B82Y 40/00 264/400 |
| 2013/0152823 A1 | 6/2013 | El-Sayed | |
| 2013/0203849 A1 | 8/2013 | Ben Yehuda | |
| 2013/0224477 A1 | 8/2013 | Xu | |
| 2013/0334104 A1 | 12/2013 | Marsh | |
| 2013/0337998 A1 | 12/2013 | Irving | |
| 2014/0274830 A1 | 9/2014 | Pol et al. | |
| 2014/0288194 A1 | 9/2014 | Niedermeyer | |
| 2014/0370293 A1 | 12/2014 | Johnson | |
| 2015/0008313 A1 | 1/2015 | Loboda | |
| 2015/0066135 A1 | 3/2015 | Weber et al. | |
| 2016/0081347 A1 | 3/2016 | Niedermeyer | |
| 2016/0082513 A1* | 3/2016 | Niedermeyer | B23K 26/1224 424/405 |
| 2016/0082514 A1 | 3/2016 | Niedermeyer | |
| 2016/0083146 A1 | 3/2016 | Niedermeyer | |
| 2016/0083665 A1 | 3/2016 | Niedermeyer | |
| 2016/0083901 A1 | 3/2016 | Niedermeyer | |
| 2016/0144350 A1 | 5/2016 | Aizenberg et al. | |
| 2016/0287631 A1 | 10/2016 | Tarbet et al. | |
| 2016/0298243 A1 | 10/2016 | Tarbet et al. | |
| 2016/0372243 A1 | 12/2016 | Cassignol | |

FOREIGN PATENT DOCUMENTS

| | | | |
|---|---|---|---|
| CN | 104014811 | 9/2014 | |
| DE | 102005044360 | 3/2007 | |
| EP | 2140958 | 1/2010 | |
| EP | 2559436 | 2/2013 | |
| JP | 2010001528 | 1/2010 | |
| KR | 20060021749 | 3/2006 | |
| WO | WO2006026026 | 3/2006 | |
| WO | WO2006053225 | 5/2006 | |
| WO | WO2006/062826 | 6/2006 | |
| WO | WO2008/043396 | 4/2008 | |
| WO | WO2009025955 | 2/2009 | |
| WO | WO2009044146 | 4/2009 | |
| WO | WO2009046081 | 4/2009 | |
| WO | WO2009091900 | 7/2009 | |
| WO | WO2011045627 | 4/2011 | |
| WO | WO2013141879 | 9/2013 | |
| WO | WO 2014066850 A2 * | 5/2014 | A01N 59/16 |
| WO | 2014137352 | 9/2014 | |
| WO | WO 2016007112 A1 * | 1/2016 | B01J 13/0043 |
| WO | WO 2016007113 A1 * | 1/2016 | B01J 13/0043 |

OTHER PUBLICATIONS

Barcikowski et al., "Generation of nanoparticle colloids by picosecond and femtosecond laser ablations in liquid flow", Appl. Phys. Lett. 91, 083113 (2007).

Chien et al., "Synthesis of nanoparticles: sunlight formation of gold nanodecahedra for ultra-sensitive lead-ion detection", Green Chem., vol. 13, pp. 1162-1166, May 2011.

International Search Report for PCT App. No. PCT/US2012/044907 dated Jan. 13, 2013.

International Search Report for PCT App. No. PCT/US2015/051642 dated Dec. 14, 2015.

International Search Report for PCT App. No. PCT/US2015/051639 dated Dec. 17, 2015.

International Search Report for PCT App. No. PCT/US2015/051640 dated Dec. 17, 2015.

International Search Report for PCT App. No. PCT/US2015/051643 dated Dec. 17, 2015.

International Search Report for PCT App. No. PCT/US2015/051649 dated Dec. 17, 2015.

International Search Report for PCT App. No. PCT/US2015/051646 dated Dec. 18, 2015.

Jacobson, "These six diseases should worry you more than Ebola", Inside Energy Oct. 2014; [online] retrieved on Jan. 29, 2017 from http://www.pbs.org/newshour/updates/six-diseases-actually-worry/; 10 pages.

Jana et al., "Seeding Growth for Size Control of 5-40 nm Diameter Gold Nanoparticles", Langmuir 2001, 17, 6782-6786.

Liu et al., "A novel coral-like porous SnO2 hollow architecture: biomimetic swallowing growth mechanism and enhanced photovoltaic (56) References Cited

OTHER PUBLICATIONS property for dye-sensitized solar cell application", Chem. Commun., vol. 46, pp. 472-474, 2010.
Mafuné et al., "Formation of Stable Platinum Nanoparticles by Laser Ablation in Water", J. Phys. Chem. B 2003, 107, 4218-4223.
Pal et al., "Does the Antibacterial Activity of Silver Nanoparticles Depend on the Shape of the Nanoparticle?", Applied and Environmental Microbiology, 2007; 73(6): 1712-1720.
Phuoc et al, "Synthesis of Ag-deoionized water nanofluids using multi-beam laser ablation in fluids", Optics and Lasers in Engineering 45 (2007) 1099-1106.
Prabhu et al., "Silver nanoparticles: mechanism of antimicrobial action, synthesis, medical applications, and toxicity effects", International Nano Letters, 2012, 2:32, pp. 1-10.
Rawashdeh et al., "Antibacterial Mechanisms of Metallic Nanoparticles: A Review", Dynamic Biochemistry, Process Biotechnology and Molecular Biology 2009 pp. 12-20.
Riabinina et al., "Influence of pressure on the Pt nanoparticle growth modes during pulsed laser ablation", Journal of Applied Physics 108, 034322 (2010, published online Aug. 12, 2010).
Sahu et al., "Flower Shaped Silver Nanostructures: An Efficient Bacteria Exterminator", A Search for Antibacterial Agents; Chapter 2; [online] retrieved from: http://www.intechopen.com/books/a-search-for-antibacterial-agents; 2007; 73(6): 1712-1720.
Santos et al., "Enhancemetn of antibiotic effect via gold:silver-alloy nanoparticles", J. Nanopart Res (2012) 14:859, pp. 1-8.
Sylvestre et al., "Surface Chemistry of Gold Nanoparticles Produced by Laser Ablation in Aqueous Media", J Phys. Chem. B 2004, 108, 16864-16869.
Sweeney et al., "Rapid Purification and Size Separation of Gold Nanoparticles via Diafiltration", J. Am. Chem. Soc. 2006, 128, 3190-3197 (Published on web Feb. 18, 2006).
U.S. Appl. No. 13/175,708, filed Jul. 1, 2011, Office Action dated May 30, 2014.
U.S. Appl. No. 13/175,708, filed Jul. 1, 2011, Final Office Action dated Nov. 13, 2014.
U.S. Appl. No. 13/175,708, filed Jul. 1, 2011, Office Action dated Jul. 6, 2015.
U.S. Appl. No. 14/861,243, filed Sep. 22, 2015, Office Action dated Mar. 9, 2016.
U.S. Appl. No. 13/175,708, filed Jul. 1, 2011, Final Office Action dated Mar. 28, 2016.
U.S. Appl. No. 14/861,318, filed Sep. 22, 2015, Office Action dated Apr. 25, 2016.
U.S. Appl. No. 14/861,318, filed Sep. 22, 2015, Notice of Allowance dated May 20, 2016.
U.S. Appl. No. 14/861,318, filed Sep. 22, 2015, Corrected Notice of Allowance dated Jun. 15, 2016.
U.S. Appl. No. 14/861,243, filed Sep. 22, 2015, Final Office Action dated Jul. 26, 2016.
U.S. Appl. No. 14/861,442, filed Sep. 22, 2015, Office Action dated Sep. 29, 2016.
U.S. Appl. No. 14/861,243, filed Sep. 22, 2015, Office Action dated Nov. 2, 2016.
U.S. Appl. No. 14/861,562, filed Sep. 22, 2015, Office Action dated Dec. 7, 2016.
U.S. Appl. No. 14/861,243, filed Sep. 22, 2015, Final Office Action dated Jan. 27, 2017.
U.S. Appl. No. 15/088,863, filed Apr. 1, 2016, Office Action dated Feb. 3, 2017.
U.S. Appl. No. 13/175,708, filed Jul. 1, 2011, Office Action dated Feb. 10, 2017.
U.S. Appl. No. 14/861,442, filed Sep. 22, 2015, Final Office Action dated Feb. 22, 2017.
U.S. Appl. No. 14/298,594, filed Jun. 6, 2014, Office Action dated Mar. 21, 2017.
Theodorou et al., "Inhalation of Silver Nanomaterials—Seeing the Risks", International Journal of Molecular Sciences, 2014, 15, 23936-23974.
U.S. Appl. No. 14/861,562, filed Sep. 22, 2015, Final Office Action dated Jun. 23, 2017.
U.S. Appl. No. 15/088,863, filed Apr. 1, 2016, Final Office Action dated Jul. 11, 2017.
U.S. Appl. No. 14/861,442, filed Sep. 22, 2015, Office Action dated Aug. 23, 2017.
U.S. Appl. No. 14/861,375, filed Sep. 22, 2015, Office Action dated Sep. 8, 2017.
U.S. Appl. No. 14/861,500, filed Sep. 22, 2015, Office Action dated Sep. 22, 2017.
U.S. Appl. No. 14/861,243, filed Sep. 22, 2015, Office Action dated Sep. 25, 2017.
U.S. Appl. No. 14/298,594, filed Jun. 6, 2014, Final Office Action dated Oct. 17, 2017.
U.S. Appl. No. 15/829,512, filed Nov. 29, 2017, Tarbet et al.
U.S. Appl. No. 14/861,243, filed Sep. 22, 2015, Final Office Action dated Feb. 2, 2018.
U.S. Appl. No. 14/861,375, filed Sep. 22, 2015, Final Office Action dated Apr. 3, 2018.
U.S. Appl. No. 15/808,088, filed Nov. 9, 2017, Niedermeyer.
U.S. Appl. No. 15/976,447, filed May 10, 2018, Niedermeyer.
U.S. Appl. No. 16/012,508, filed Jun. 19, 2018, Niedermeyer.
Malvern, "The use of the Malvern Zetasizer for the measurement of Zeta Potential", article from the Internet, http://www.malvern.co.alLaboratory/zetaintm.htm> 10 pages, printed on Feb. 12, 2002.
Malvern, "Zeta Potential Theory, Dispersion stability", article from the Internet, http://www.malvern.co.uk/Laboratory/zettheo.htm >, 3 pages, printed on Feb. 12, 2002.
NOAA Ocean Service Education, "Corals", downloaded from https://oceanservice.noaa.gov/education/kits/corals/coral03_growth.html on Sep. 5, 2017.
Leisure Pro, "Coral Identification: Types of Coral (Part 1-Hard Coral)", downloaded from http://www.leisurepro.com/blog/explorethe-blue/coral-identification-types-of-coral-part-1 on Sep. 2017.
International Coral Reef Initiative, "What are Corals", downloaded from http://www.iciforum.org/about-coral-reefs/what-are-corals on Sep. 5, 2017.
U.S. Appl. No. 15/415,562, May 23, 2017, Office Action cited in U.S. Appl. No. 15/415,562 dated May 23, 2017.
U.S. Appl. No. 15/415,562, Sep. 5, 2017, Office Action cited in U.S. Appl. No. 15/415,562 dated Sep. 5, 2017.
U.S. Appl. No. 15/415,562, Jan. 31, 2018, Office Action cited in U.S. Appl. No. 15/415,562 dated Jan. 31, 2018.

* cited by examiner

FIG. 5 ns and methods for treating onychomycosis, including stabilized multi-component anti-fungal nanoparticle compositions for treating onychomycosis and methods for making and using such compositions.

NANOPARTICLE COMPOSITIONS AND METHODS FOR TREATING ONYCHOMYCOSIS

CROSS-REFERENCE TO RELATED APPLICATIONS

This application claims the benefit of U.S. Provisional Patent Application No. 62/286,768, filed Jan. 25, 2016, the disclosure of which is incorporated herein in its entirety.

BACKGROUND

1. Field of the Invention

Disclosed herein are nanoparticle compositions and methods for treating onychomycosis, including stabilized multi-component anti-fungal nanoparticle compositions for treating onychomycosis and methods for making and using such compositions.

2. Relevant Technology

Onychomycosis is a fungal infection of the fingernail or toenail. These infections can range from mild but annoying to painful and inflamed. For some, such as those who are immunocompromised (e.g., due to medication, AIDS, diabetes, cancer, leukemia, or cancer treatment), an untreated infection can progress to a serious and even life threatening state. Additionally, such infections can negatively affect one's desired appearance and can lead to cosmetic concerns, with infected nails becoming thick, brittle, and discolored, with the potential for permanent damage to the infected nails. Further, some who have onychomycosis may also suffer from associated skin rashes, lesions, or other dermal irritations as a result of an allergic reaction to the fungus underlying the onychomycosis.

Treatment of onychomycosis is typically carried out by eliminating the underlying microbial cause of the condition. Fungi that are typically associated with onychomycosis include dermatophytes, yeasts such as *Candida albicans*, and nondermatophytic molds. However, antifungal therapy is often difficult, owing to the fact that fungi are eukaryotic organisms that do not respond to antibiotics, limiting the number of compounds useful against the underlying fungi. In addition, the infection is typically embedded deep within the nail, making it difficult to provide contact of the treatment compound to the infection. Also, because nail growth is relatively slow, it may take an extended period of time (e.g., up to a year or more in some cases) for older, infected portions of the nail to move to a location where treatment is more feasible. For treatments that must typically be applied daily, if not more frequently, compliance over such an extended period of time becomes extremely difficult. In some cases, removal of all or part of the nail may be recommended or required, which can be painful to the patient.

Accordingly, there has been and remains a need to find reliable treatments for use in treating onychomycosis. Such treatments should be able to reliably kill or deactivate the underlying fungal infection causing the disease without causing unnecessary pain or undue harm to the organism being treated (e.g., human or animal).

BRIEF SUMMARY

Disclosed herein are nanoparticle compositions and treatment methods for treating and/or preventing onychomycosis. One or more embodiments can include: spherical-shaped metal nanoparticles having a particle size and a particle distribution; coral-shaped metal nanoparticles having a particle size and a particle size distribution; and a penetrating solvent configured to deliver the nanoparticles to a target area of a nail and/or surrounding tissue. For example, the penetrating solvent can be configured to deliver the nanoparticles to an infected area of the nail and/or surrounding tissue so as to kill or otherwise deactivate the fungal microbes underlying the onychomycosis.

One or more embodiments relate to a method of treating or preventing onychomycosis, including: applying a nanoparticle composition to a nail or surrounding tissue; and the nanoparticle composition killing or deactivating fungal microbes contacted with the nanoparticle composition.

One or more embodiments relate to a method of manufacturing a nanoparticle composition for treating onychomycosis, including: obtaining spherical-shaped nanoparticles; obtaining coral-shaped nanoparticles; and combining the spherical-shaped nanoparticles and the coral-shaped nanoparticles in a penetrating solvent, the penetrating solvent being configured to deliver the nanoparticles to a target area of a nail and/or surrounding tissue.

DETAILED DESCRIPTION

Disclosed herein are nanoparticle compositions and methods for treating and preventing onychomycosis. Also disclosed herein are nanoparticle compositions and methods for preventing infection or further infection of nails, leading to onychomycosis. Also disclosed are methods for making and using such nanoparticle compositions.

Unexpectedly, it has been found that in some embodiments, by selecting at least two differently configured metal nanoparticle components (e.g., different in size, shape, or both), each with specific particle size distribution, and mixing those at least two nanoparticle components with a highly penetrating solvent (e.g., dimethyl sulfoxide), it is possible to effectively kill and/or deactivate fungal microbes underlying an onychomycosis condition.

Nanoparticle Configurations

In some embodiments, the metal nanoparticles may comprise or consist essentially of nonionic, ground state metal nanoparticles. Examples include spherical-shaped metal nanoparticles, coral-shaped metal nanoparticles, or a blend of spherical-shaped metal nanoparticles and coral-shaped metal nanoparticles.

In some embodiments, metal nanoparticles useful for making nanoparticle compositions comprise spherical nanoparticles, preferably spherical-shaped metal nanoparticles having a solid core. The term "spherical-shaped metal nanoparticles" refers to nanoparticles that are made from one or more metals, preferably nonionic, ground state metals, having only internal bond angles and no external edges or bond angles. In this way, the spherical nanoparticles are highly resistant to ionization, highly stable, and highly resistance to agglomeration. Such nanoparticles can exhibit a high ξ-potential, which permits the spherical nanoparticles to remain dispersed within a polar solvent without a surfactant, which is a surprising and unexpected result.

In some embodiments, spherical-shaped metal nanoparticles can have a diameter of about 40 nm or less, about 35 nm or less, about 30 nm or less, about 25 nm or less, about 20 nm or less, about 15 nm or less, about 10 nm or less, about 7.5 nm or less, or about 5 nm or less.

In some embodiments, spherical-shaped nanoparticles can have a particle size distribution such that at least 99% of the nanoparticles have a diameter within 30% of the mean diameter of the nanoparticles, or within 20% of the mean diameter, or within 10% of the mean diameter. In some embodiments, spherical-shaped nanoparticles can have a mean particle size and at least 99% of the nanoparticles have a particle size that is within ±3 nm of the mean diameter, ±2 nm of the mean diameter, or ±1 nm of the mean diameter. In some embodiments, spherical-shaped nanoparticles can have a ξ-potential (measured as an absolute value) of at least 10 mV, preferably at least about 15 mV, more preferably at least about 20 mV, even more preferably at least about 25 mV, and most preferably at least about 30 mV.

Examples of methods and systems for manufacturing spherical-shaped nanoparticles are disclosed in U.S. Pat. Pub. No. 2013/0001833 to William Niedermeyer, incorporated herein by this reference.

Figure 1A:
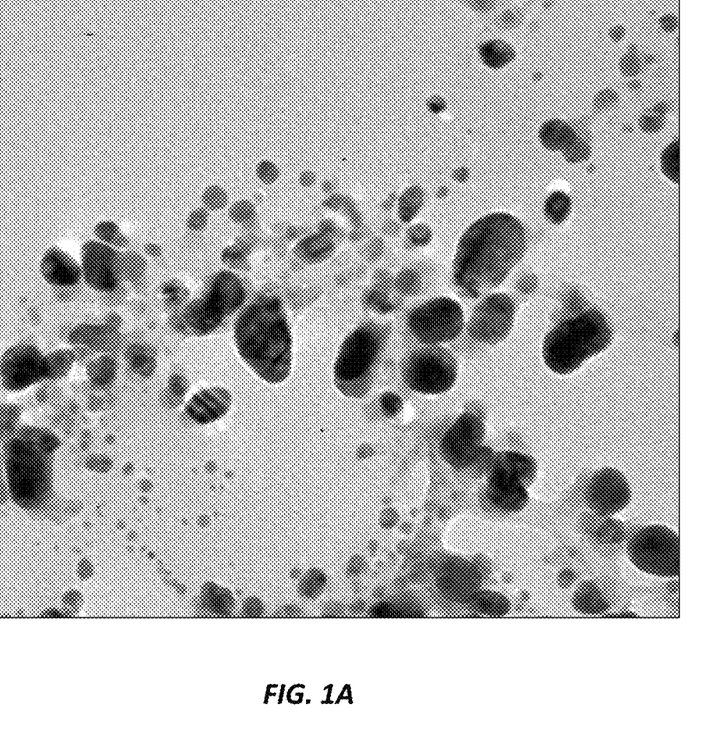
FIGS. 1A-1D show transmission electron microscope (TEM) images of nanoparticles made according to standard chemical synthesis methods.
Figure 1B:
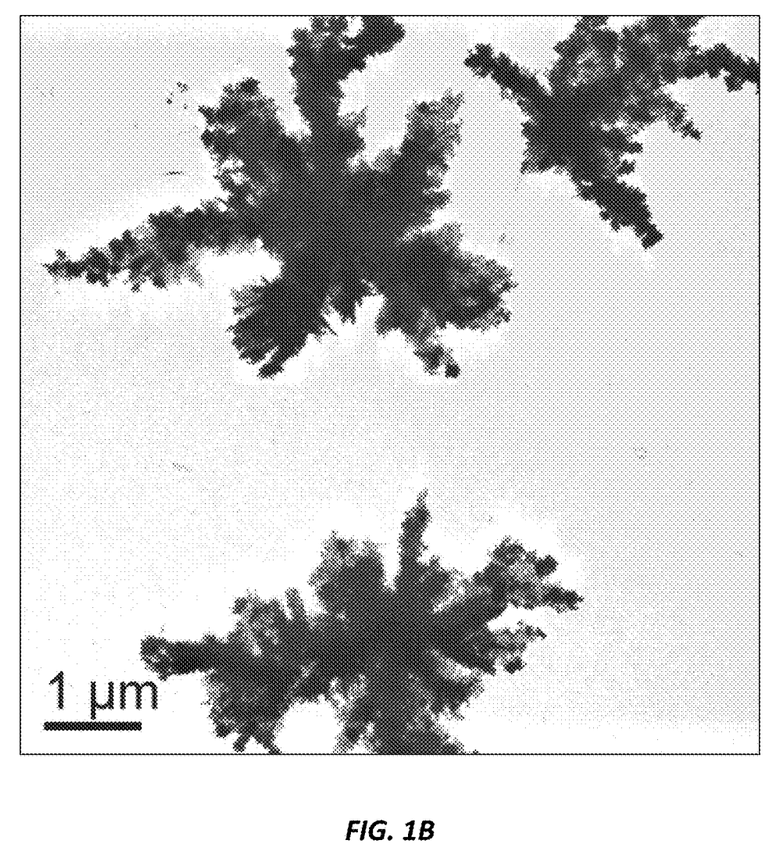
Figure 1C:
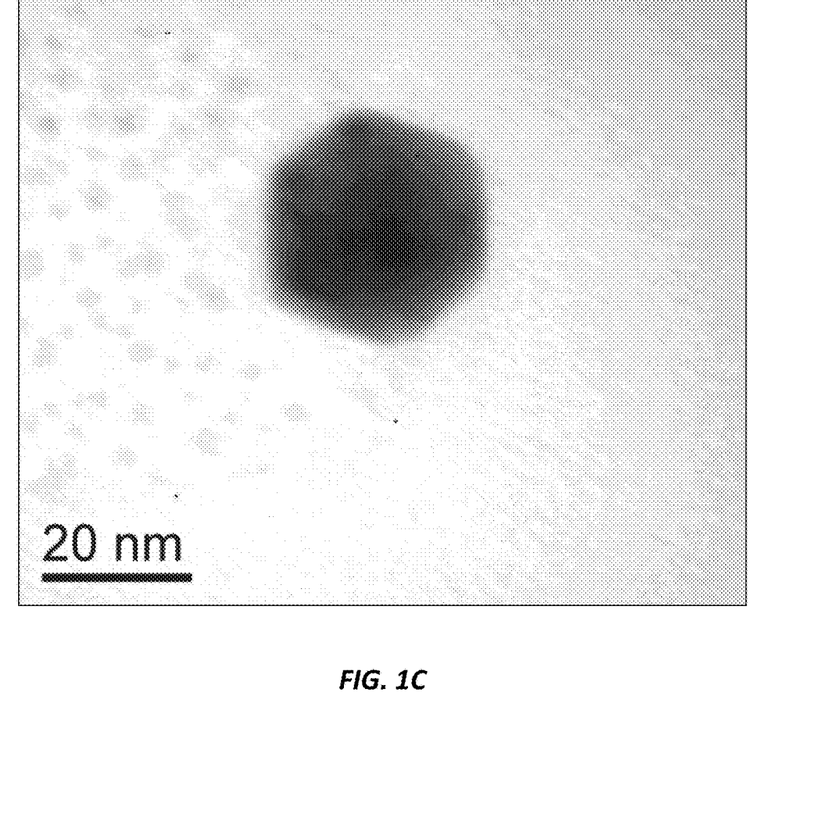
Figure 1D:
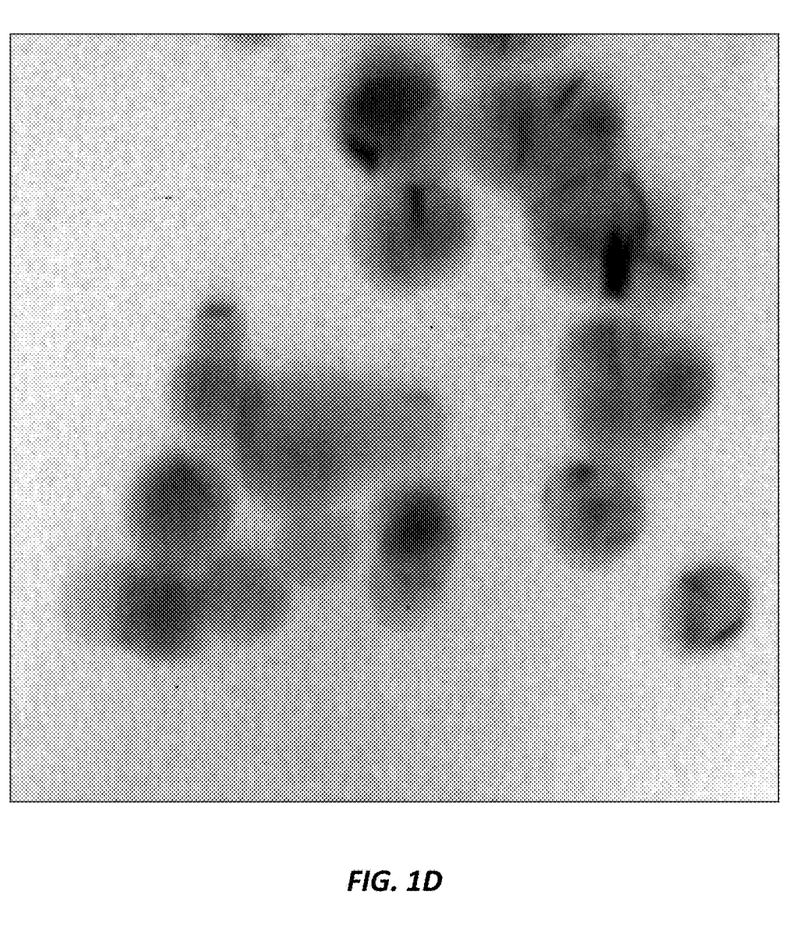

FIGS. 1A-1D show transmission electron microscope (TEM) images of nanoparticles made according to various chemical synthesis methods. As shown, the nanoparticles formed using these various chemical synthesis methods tend to exhibit a clustered, crystalline, or hedron-like shape rather than a true spherical shape with round and smooth surfaces. For example, FIG. 1A shows silver nanoparticles formed using a common trisodium citrate method. The nanoparticles are clustered and have a relatively broad size distribution. FIG. 1B shows another set of silver nanoparticles (available from American Biotech Labs, LLC) formed using another chemical synthesis method and showing rough surface morphologies with many edges. FIG. 1C shows a gold nanoparticle having a hedron shape as opposed to a truly spherical shape. FIG. 1D shows a set of silver nanoparticles (sold under the trade name MesoSilver), which have relatively smoother surface morphologies but are understood to be shells of silver formed over a non-metallic seed material.

Figure 2A:
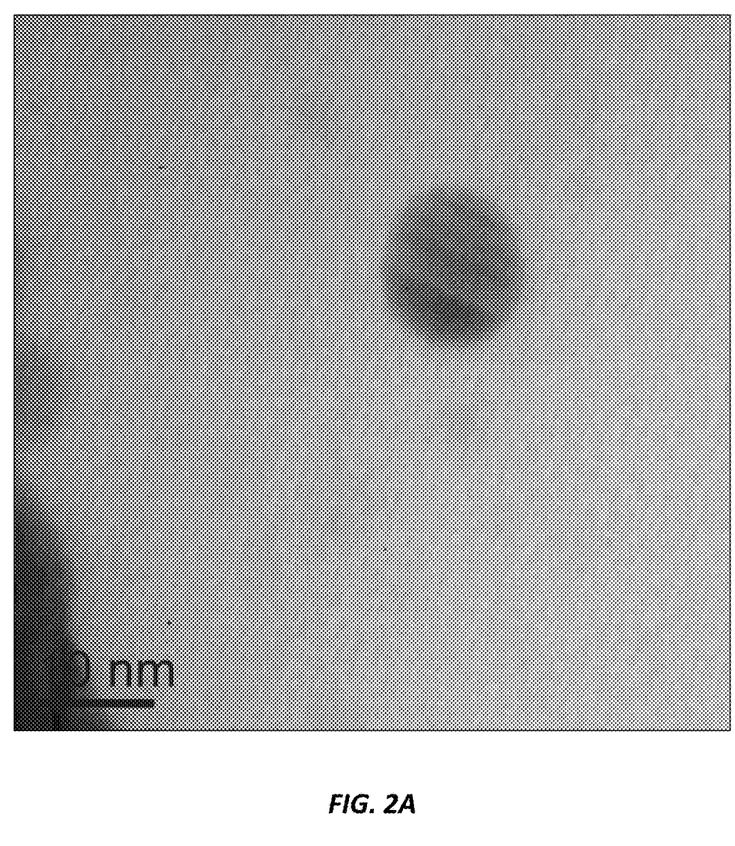
FIGS. 2A-2C show TEM images of exemplary spherical-shaped metal nanoparticles having substantially uniform size and narrow particle size distribution, smooth surface morphology, and solid metal core, for use in making nanoparticle compositions for treating onychomycosis.
Figure 2B:
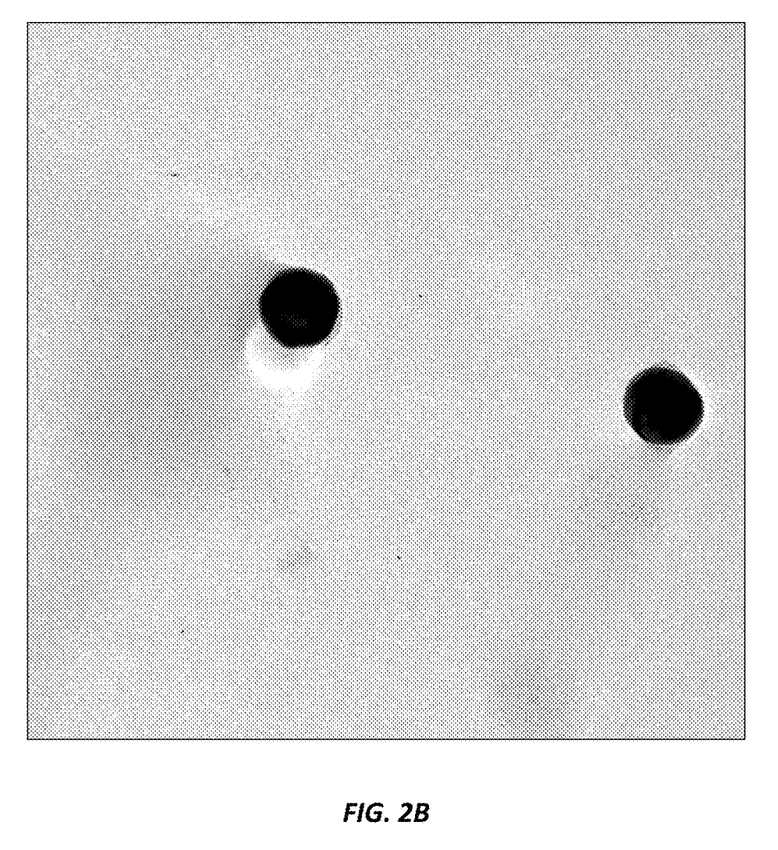
Figure 2C:
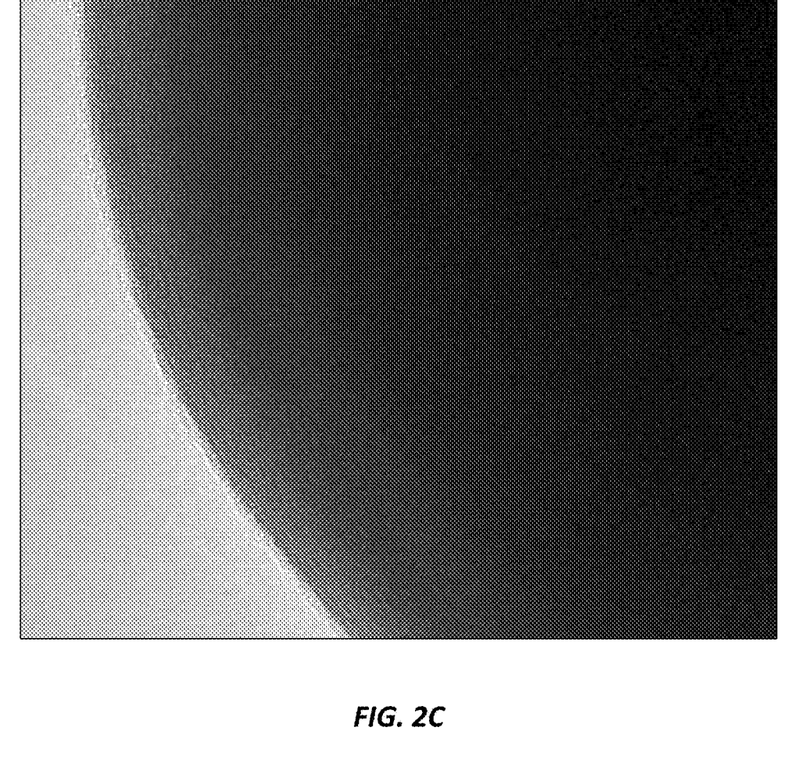

In contrast, the spherical-shaped nanoparticles described herein are solid metal, substantially unclustered, and have a smooth and round surface morphology along with a narrow size distribution. FIGS. 2A-2C show TEM images of spherical-shaped nanoparticles utilized in embodiments of the present disclosure. FIG. 2A shows a gold/silver alloy nanoparticle (90% silver and 10% gold by molarity). FIG. 2B shows two spherical nanoparticles side by side to visually illustrate size similarity. FIG. 2C shows a surface of a metal nanoparticle showing the smooth and edgeless surface morphology.

In some embodiments, nonionic metal nanoparticles useful for making nanoparticle compositions may also comprise coral-shaped nanoparticles. The term "coral-shaped metal nanoparticles" refers to nanoparticles that are made from one or more metals, preferably nonionic, ground state metals having a non-uniform cross section and a globular structure formed by multiple, non-linear strands joined together without right angles. Similar to spherical-shaped nanoparticles, coral-shaped nanoparticles may have only internal bond angles and no external edges or bond angles. In this way, coral-shaped nanoparticles can be highly resistant to ionization, highly stable, and highly resistance to agglomeration. Such coral-shaped nanoparticles can exhibit a high ξ-potential, which permits the coral-shaped nanoparticles to remain dispersed within a polar solvent without a surfactant, which is a surprising and unexpected result.

In some embodiments, coral-shaped nanoparticles can have lengths ranging from about 15 nm to about 100 nm, or about 25 nm to about 95 nm, or about 40 nm to about 90 nm, or about 60 nm to about 85 nm, or about 70 nm to about 80 nm. In some embodiments, coral-shaped nanoparticles can have a particle size distribution such that at least 99% of the nanoparticles have a length within 30% of the mean length, or within 20% of the mean length, or within 10% of the mean length. In some embodiments, coral-shaped nanoparticles can have a ξ-potential of at least 10 mV, preferably at least about 15 mV, more preferably at least about 20 mV, even more preferably at least about 25 mV, and most preferably at least about 30 mV.

Examples of methods and systems for manufacturing coral-shaped nanoparticles are disclosed in U.S. Pat. Pub. No. 2016/0082514 to William Niedermeyer, which is incorporated by this reference.

The metal nanoparticles, including spherical-shaped and/or coral-shaped nanoparticles, may comprise any desired metal, mixture of metals, or metal alloy, including at least one of silver, gold, platinum, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, or alloys thereof.

Antifungal Activity

Figure 3:
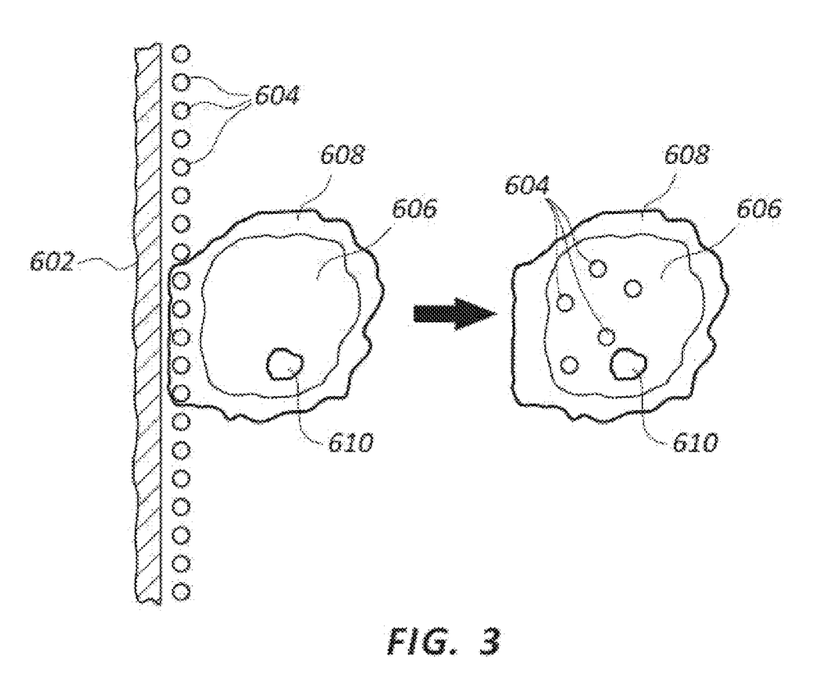
FIG. 3 schematically illustrates a microbe after having absorbed spherical-shaped metal nanoparticles.

FIG. 3 schematically illustrates a fungal microbe 608 having absorbed spherical-shaped nanoparticles 604 from a solid substrate 602 (e.g., a portion of fingernail or toenail tissue), such as by active absorption or other transport mechanism. Alternatively, spherical-shaped nanoparticles 604 can be provided in a composition (not shown), such as in a liquid or gel carrier. The nanoparticles 604 can freely move throughout the interior 606 of microbe 608 and come into contact with one or more vital proteins or enzymes 610 that, if denatured, will kill or disable the microbe.

Figure 4:
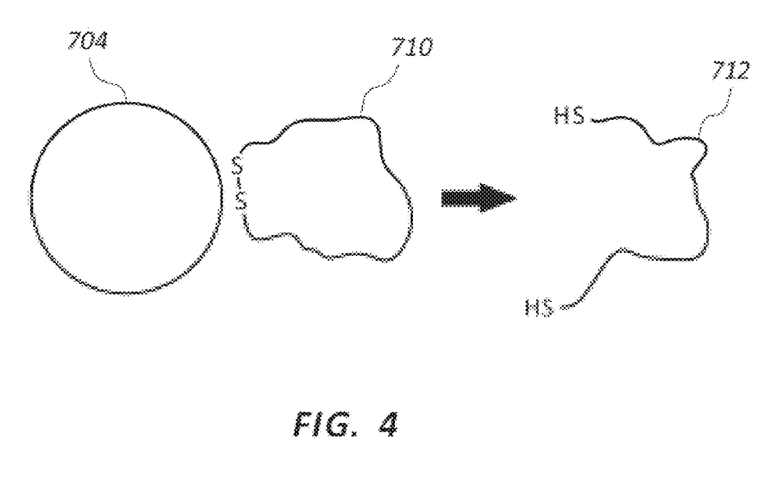
FIG. 4 schematically illustrates a microbe protein with disulfide bonds being catalytically denatured by an adjacent spherical-shaped nanoparticle.

One way that nanoparticles may kill or denature a fungal microbe is by catalyzing the cleavage of disulfide (S—S) bonds within a vital protein or enzyme. FIG. 4 schematically illustrates a microbe protein or enzyme 710 with disulfide bonds being catalytically denatured by an adjacent spherical-shaped nanoparticle 704 to yield denatured protein or enzyme 712. The cleavage of disulfide bonds and/or cleavage of other chemical bonds of vital proteins or enzymes may occur within the cell interior, thereby killing the microbe in this manner. Such catalytic cleavage of disulfide (S—S) bonds is facilitated by the generally simple protein structures of most fungi, in which many vital disulfide bonds are exposed and readily cleaved by catalysis.

Another mechanism by which metal (e.g., silver) nanoparticles can kill microbes is through the production of active oxygen species, such as peroxides, which can oxidatively cleave protein bonds, including but not limited to amide bonds.

Figure 5:
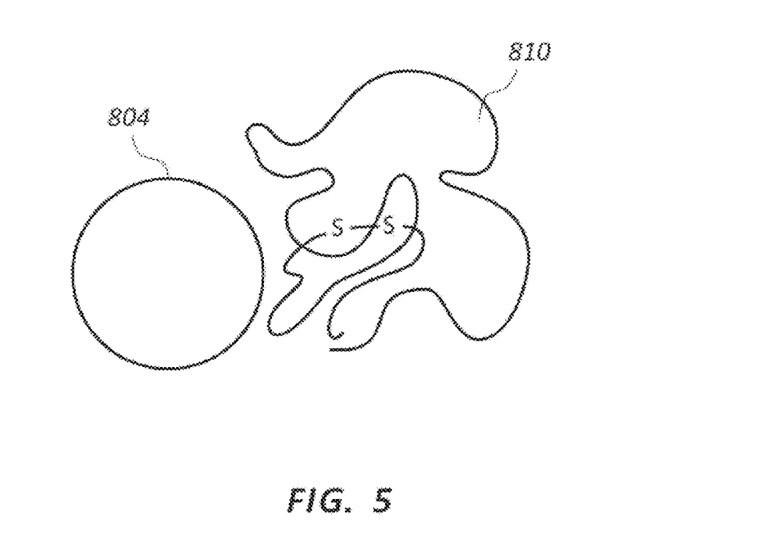
FIG. 5 schematically illustrates a mammalian protein with disulfide bonds that are shielded so as to resist being catalytically denatured by an adjacent spherical-shaped nanoparticle.

Notwithstanding the lethal nature of nonionic metal nanoparticles relative to fungi, they can be relatively harmless to humans, mammals, and healthy mammalian cells, which contain much more complex protein structures compared to simple fungal microbes and in which most or all vital disulfide bonds are shielded by other, more stable regions of the protein. FIG. 5 schematically illustrates a mammalian protein 810 with disulfide (S—S) bonds that are shielded so as to resist being catalytically denatured by an adjacent spherical-shaped nanoparticle 804. In many cases the nonionic nanoparticles do not interact with or attach to human or mammalian cells, remain in and follow fluid flow, do not cross barriers, remain in the vascular system, and can be quickly and safely expelled through the urine without damaging kidneys or other cells.

Beneficially, the interaction of the metal nanoparticles with fungal microbes has been demonstrated to be lethal to the fungal microbes without relying on or producing metal ions. In the particular case of silver (Ag) nanoparticles, the interaction of the silver (Ag) nanoparticle(s) with a fungal microbe has been demonstrated to be particularly lethal without the need to rely on the production of silver ions ($Ag^+$) to provide the desired antifungal effects, as is typically the case with conventional colloidal silver compositions. The ability of nonionic nanoparticles as described herein (e.g., silver (Ag) nanoparticles) to provide effective antifungal control without any significant release of toxic metal ions (e.g., silver ions ($Ag^+$)) into the surrounding environment is a substantial advancement in the art.

Targeted Nanoparticles

In preferred embodiments, anti-fungal compositions can include metal nanoparticles having a particle size of about 9 nm to about 20 nm, or about 10 nm to about 18 nm, or about 11 nm to about 16 nm, or about 12 nm to about 15 nm. Within any of the foregoing size ranges, it is possible to select "designer antifungal particles" of specific size that are particularly effective in targeting a specific fungus.

The ability to select and use fungus-specific nanoparticles provides a number of benefits. For example, in the case where only certain nanoparticle sizes are effective in killing a particular fungus or class of fungi, such as those responsible for onychomycosis, providing metal nanoparticles within a narrow particle size distribution of the correct particle size maximizes the proportion of nanoparticles that are effective in killing the target microbe and minimizes the proportion of nanoparticles that are less effective, or ineffective, in killing the target microbe. This, in turn, greatly reduces the overall amount or concentration of nanoparticles required to provide a desired kill or deactivation rate of a targeted microbe. Eliminating improperly sized nanoparticles also reduces the tendency of the composition to kill or harm non-targeted microbes or other cells, such as healthy mammalian cells. In this way, highly specific antifungal compositions can better target a harmful microbe while being less harmful or even non-toxic to humans and animals.

In some embodiments, for example, the nanoparticles can have a particle size in a range of about 1 nm to about 25 nm, or about 2 nm to about 15 nm, or about 2 nm to about 7 nm, or about 3 nm to about 6 nm, or about 7 nm to about 11 nm, or about 11 nm to about 14 nm.

By way of further example, nanoparticles having a diameter of about 12 nm to about 18 nm (e.g., 12-15 nm) have been found to be effective in killing fungi. Within the foregoing ranges, there may be specific sizes of nanoparticles that are most effective in killing particular types of fungi.

Multi-Component Nanoparticle Compositions

In some embodiments, coral-shaped metal nanoparticles can be used in conjunction with spherical-shaped metal nanoparticles. In general, spherical-shaped metal nanoparticles can be smaller than coral-shaped metal nanoparticles and in this way can provide very high surface area for catalyzing desired reactions or providing other desired benefits. On the other hand, the generally larger coral-shaped nanoparticles can exhibit higher surface area per unit mass compared to spherical-shaped nanoparticles because coral-shaped nanoparticles have internal spaces and surfaces rather than a solid core and only an external surface. In some cases, providing nanoparticle compositions containing both spherical-shaped and coral-shaped nanoparticles can provide synergistic results. For example, coral-shaped nanoparticles can help carry and/or potentiate the activity of spherical-shaped nanoparticles in addition to providing their own unique benefits.

In some embodiments, the nanoparticle compositions may include both spherical-shaped and coral-shaped nanoparticles. In some embodiments, the mass ratio of spherical-shaped nanoparticles to coral-shaped nanoparticles in the nanoparticle composition can be in a range of about 1:1 to about 50:1, or about 2.5:1 to about 25:1, or about 5:1 to about 20:1, or about 7.5:1 to about 15:1, or about 9:1 to about 11:1, or about 10:1. The particle number ratio of spherical-shaped nanoparticles to coral-shaped nanoparticles in the nanoparticle composition can be in a range of about 10:1 to about 500:1, or about 25:1 to about 250:1, or about 50:1 to about 200:1, or about 75:1 to about 150:1, or about 90:1 to about 110:1, or about 100:1.

In some embodiments, an antimicrobial composition may comprise (1) a first set of metal nanoparticles having a specific particle size and a particle size distribution, (2) and second set of metal nanoparticles having a specific particle size and a particle size distribution, and (3) a penetrating solvent.

Other embodiments can additionally include (4) a stabilizing agent and/or (5) a carrier. The penetrating solvent, stabilizing agent, and/or carrier may be comprised of one or more other components for delivery of the multicomponent nanoparticles onto and ultimately into the nail region of a person or animal.

Because of the extremely small size and spherical shape of the spherical nanoparticles it is believed that these particles are absorbed into and move quickly through the dermal and/or nail region of an animal or human. Unexpectedly, while the coral-shaped nanoparticles alone have not exhibited significant antifungal efficacy (relative to the spherical nanoparticles), the inclusion of these particles in conjunction with specifically sized spherical nanoparticles has provided increased efficacy for the spherical particles.

In some embodiments, the compositions will include at least one spherical-shaped nanoparticle component and a larger coral-shaped nanoparticle component. In these embodiments, the at least one selected spherical-shaped nanoparticle component will be present in the solution in a range of between about 1 and about 15 ppm (e.g., at least 1 and at most 15 ppm) and more particularly in the range of between bout 1 and about 5 ppm (e.g., at least 1 and at most 5 ppm). Additionally, in some embodiments, the larger coral-shaped nanoparticles will be present in the solution in a range of between about 1 and about 5 ppm (e.g., at least 1 and at most 5 ppm) and more particularly between about 1 and about 3 ppm (e.g., at least 1 and at most 3 ppm). It should be understood that the upper concentration is not restricted as much by efficacy, as by product formulation cost. Thus, in other embodiments, the spherical-shaped nanoparticle component may present at a concentration above 5 ppm and/or the coral-shaped nanoparticle component may be present at a concentration above 3 ppm.

According to some embodiments, the spherical antimicrobial metal nanoparticles will comprise at least one of silver or gold. In some embodiments, the metal nanoparticles may primarily or exclusively comprise silver. However, in other embodiments, the metal nanoparticles may primarily or exclusively comprise gold. Due to the nature of silver and gold atoms making up the nanoparticles, it has been found that gold nanoparticles are typically better able to hold together at very small sizes (e.g., smaller than about 5-7 nm) compared to silver nanoparticles. On the other hand, a gold-silver alloy typically provides the particle stabilizing activity of gold and the higher microbe killing activity of silver.

In some embodiments, the coral-shaped nanoparticles will primarily or exclusively include gold nanoparticles.

Penetrating Solvent

Some embodiments may include a penetrating solvent configured to promote delivery of the nanoparticles through the nail or partially through the nail in order to reach the microbes causing the fungal infection. In some embodiments, the penetrating solvent can be an organic solvent, such as an alcohol (e.g., methanol, ethanol, butanol, etc.), ketone (e.g., acetone), and/or ester (e.g., mono-, di-, and triglycerides, alkyl alkanoates such as ethyl acetate and isopropyl myristate).

In some embodiments, the penetrating solvent can include one or more fatty acids (e.g., oleic acid, myristoleic acid, palmitoleic acid, sapienic acid, elaidic acid, vaccenic acid, erucic acid, arachidonic acid, linoleic acid, linoelaidic acid, linolenic acid, and other fatty acids).

In some embodiments, the penetrating solvent can include one or more diols, such as propylene glycol, propane-1,3-diol, ethylene glycol, and/or polyethylene glycol. In some embodiments, one or more dials can be combined with one or more fatty acids to enhance a penetrating effect. For example, in some embodiments, the penetrating solvent can include propylene glycol and oleic acid.

In some embodiments, the penetrating solvent can include one or more amines, such as triethylamine and/or ethylenediaminetetraacetic acid (EDTA). In some embodiments, the penetrating effect can be augmented by addition of EDTA.

In some embodiments, the penetrating solvent can include one or more surfactants, including nonionic surfactants such as polysorbates, polyethoxylated alkyl ethers, and/or poloxamers (e.g., poloxamer 407).

In some embodiments, the penetrating solvent can include an alkane, such as pentane, hexane, heptane, and/or other alkanes. In some embodiments, the penetrating solvent can include toluene, benzene, xylene, and/or other benzene or toluene derivatives.

In preferred embodiments, the penetrating solvent includes dimethyl sulfoxide ("DMSO"). In other embodiments, the penetrating solvent can include one or more other dialkyl sulfoxide compounds and/or compounds containing one or more sulfinyl groups.

The penetrating solvent can be provided in an amount sufficient to provide desired penetrating effects. For example, the penetrating solvent can be mixed with water (or another organic solvent in which the penetrating solvent is miscible) to a desired concentration (e.g., about 10, 20, 30, 40, 50, 60, 70, 80, or 90% v/v, or within a range with endpoints defined by any two of the foregoing values). In some embodiments, the penetrating solvent can also function as a stabilizing agent and/or carrier (described in more detail below).

Stabilizing Agent

Some embodiments may include a stabilizing agent, For example, some embodiments may include different specifically sized nanoparticles within the same solution to take advantage of each of the different properties and effects of the different particles. However, when differently sized particles are mixed into a single solution, the overall long-term stability of these particles within that single solution may be substantially diminished as a result of unequal forces exerted on the various particles causing eventual agglomeration of the particles. This phenomenon may become even more pronounced when that solution is either heated or cooled significantly above or below standard room temperature conditions. One or more stabilizing agents may be included in such embodiments to reduce or eliminate agglomeration of the nanoparticles. In some embodiments, the penetrating solvent and/or a carrier can act as the stabilizing agent. In other embodiments, a stabilizing agent may be added as a separate component to provide or enhance a stabilizing effect.

Examples of stabilizing agents include alcohols (e.g., ethanol, propanol, butanol, etc.). A more particular example of stabilizing agents include polyphenols (e.g., natural-based polyphenols such as arjuna bark extract, grape seed extract, etc.) which can have particular advantages in topical applications. In a further example, mono- or di-glycerides, or triglycerides such as grape seed oil, coconut oil, and the like, and other oils such as lavender and other terpenes may be used as stabilizing agent or part of the stabilizing agent. In addition, amine compounds such as mono-, di-, and triethanol amine, and carbohydrates such as sucrose, fructose, and higher polymers also have the ability to stabilize multi-component nanoparticle compositions and can be used as stabilizing agent or part thereof.

Stabilizing agents such as natural-based polyphenols (which would include compounds such as grape seed oil, grape seed extract (e.g., the water-soluble portion), arjuna bark extract, ethanol amines, or any other water soluble polyphenol sources and the like), can be dissolved into a carrier (e.g., water, alcohol, water alcohol combination). These natural-based polyphenols typically show good efficacy when dissolved within a carrier in the micro- to milli-molar concentrations range with the upper range limitation typically being constrained not by efficacy but by product cost.

Additional examples of stabilizing agents include liposomes, creams, and other emulsions. These and similar examples can stabilize the multi-component nanoparticle compositions while constituting the majority of the overall composition, which overall composition may contain little or no water or alcohol or other liquid-phase components.

These various stabilizing agents have the capacity to hold the at least two differently sized and/or shaped nanoparticles in suspension and deliver these nanoparticles into the treatment area of a person or animal without so powerfully retaining the nanoparticles so as to diminish the antimicrobial properties of the nanoparticles.

Carriers

Given the ability of many of these penetrating solvents and/or stabilizing agents to readily dissolve into water, alcohols, and/or oils, introduction or manufacture of the particles into solution with a penetrating solvent and/or stabilizing agent allows the nanoparticle compositions to be readily incorporated into a number of carriers that may then become the basis for a wide array of products including solvents, solutions, emulsions, suspensions, topical sprays, creams, powders, gels, pastes, and wiping solutions.

In some embodiments, the nanoparticle composition may include a carrier separate from a stabilizing agent and/or penetrating solvent, or in other embodiments a penetrating agent and/or stabilizing agent may itself function as a carrier for delivering the metal nanoparticles to a treatment area. The carrier can be a liquid, gel, or solid. Some carriers may be more suitable than others depending on the condition, location, or progression of the infection being treated. For example, the solubility characteristics of the carrier can be selected to maximize or otherwise provide a desired diffusion throughout a segment of affected tissue (such as nail tissue).

Examples of compounds that can be utilized for topical applications and can be used as carriers to formulate nanoparticle compositions in accordance to the present invention include, but are not limited to, water, alcohols, ketones, esters, citrus oils, essential oils, vegetable and other plant and natural oils, triglycerides, ethers, organic solvents, methanol, ethanol, isopropyl alcohol, other alcohols, glycols, glycerin, polyols, 1,3-propandiol, petroleum jelly, waxes, polymers, polymerizable materials, powders (e.g., talcum powder and/or cornstarch), and surfactants.

In one embodiment the carrier may be a cream or lotion including a glycerin and/or stearic acid cream base optionally containing oils such as coconut oil, olive oil, grape seed oil, shea butter, mango butter, and/or vitamin E oil along with an emulsifying wax. Such a carrier composition can also act as the stabilizing agent to maintain the nanoparticles within the cream or lotion.

Gels known in the art can be used as carriers, such as gels containing one or more of the foregoing liquid components together with known gelling agents. Gel compositions can more easily adhere to a living or non-living substrate being treated.

In some embodiments, a nanoparticle composition can be formulated so that the metal nanoparticles are included in a concentration so that a measured quantity of the nanoparticle composition, when applied to the nail or surrounding tissue, will provide a predetermined concentration or quantity of metal nanoparticles and/or will provide ongoing antimicrobial efficacy for an extended period of time. The nanoparticle composition can have a higher concentration of nanoparticles that become diluted when mixed with other liquids applied to or naturally contained on or within the nail or surrounding skin at the treatment site. Depending on the treatment site, the nature of the nanoparticles being added, and the type of penetrating solvent, stabilizing agent, and/or carrier being used, the nanoparticle composition may contain about 0.5 ppm to about 100 ppm of metal nanoparticles by weight, or about 1 ppm to about 50 ppm, or about 2 ppm to about 25 ppm, or about 3 ppm to about 20 ppm metal nanoparticles by weight.

In some embodiments, the nanoparticle composition can also include one or more optional components or adjuvants to provide desired properties, including, but not limited to antimicrobial agents, skin conditioners, plant extracts (e.g., arjuna bark extract, grape seed extract), astringents (e.g., witch hazel), moisturizers, emollients, antiseptics, and the like.

Methods of Treatment

In some embodiments, a method of treating onychomycosis comprises: (1) applying a treatment composition to a nail and/or surrounding tissue affected by a fungal infection, and (2) the treatment composition killing or deactivating the fungal microbes underlying and/or causing the infection.

In some embodiments, a method of preventing onychomycosis comprises: (1) applying a treatment composition to a nail and/or surrounding tissue, and (2) the treatment composition killing or deactivating fungal microbes present at or coming into contact with the nail and/or surrounding tissue.

Nanoparticle compositions of the present disclosure may be administered through a variety of different routes, including topical application of a cream, gel, ointment, powder, spray, liquid, paste, or other formulation. In some embodiments, the nanoparticle composition may include a penetrating solvent (e.g., dimethyl sulfoxide) configured to provide or augment delivery of the nanoparticles to the site of infection (e.g., to deeper parts of the nail and/or through the nail and into the nail bed).

The treatment composition may include spherical-shaped nanoparticles, coral-shaped nanoparticles, or both. In some embodiments, the treatment composition is a multi-component composition including a spherical-shaped nanoparticle component, a coral-shaped nanoparticle component, and a penetrating solvent.

In some embodiments, the treatment is repeated one or more times, or a subsequent, different treatment or combination of treatments is subsequently applied. For example, a treatment may an increasing or decreasing nanoparticle exposure, such as having a progressively changing nanoparticle concentration with each application to the dermatological condition. The time period between applications may also be established. For example, a nanoparticle composition may be applied weekly, every few days (e.g., five, four, three), every other day, daily, or multiple times per day (e.g., about ten, eight, six, four, or two times per day, or about every hour). In other embodiments, the nanoparticle composition may be applied as needed.

In some embodiments, a method of treating onychomycosis comprises: (1) applying a treatment composition to a nail and/or surrounding tissue, the treatment composition having (i) between about 1 and about 10 ppm of a group of spherical metal nanoparticles having a particle size of about 9 nm to about 20 nm, or about 10 nm to about 18 nm, or about 11 nm to about 16 nm, or about 12 nm to about 15 nm, (ii) optionally between about 1 and 10 ppm of a second group of coral metal nanoparticles having a particle size between 40 and 100 nm and (iii) a penetrating solvent, and (2) the anti-fungal composition killing the fungus.

Methods of Manufacture

The preferred embodiment for manufacturing the stabilized multi-component antimicrobial nanoparticle compositions requires manufacturing both nanoparticle components (e.g., in embodiments including two separate nanoparticle components) in liquids that are compatible with the final composition.

For example, in the case of a water, alcohol, or water and alcohol based composition, both the first and second nanoparticle components are manufactured in a water, alcohol, or water and alcohol based solution, and the stabilizing agent is then added to one or both of the nanoparticle components and the nanoparticle components can then be combined to achieve the desired concentrations.

In another example, such as in an embodiment having a cream based composition, the first and second nanoparticle components can be either manufactured into one of the major components of the final composition or made in a water or alcohol (or water alcohol mixture) and diluted into the cream based composition.

For example, stearic acid and oils and emulsifying wax and other minor components may be heated to between 160 and 200° F. in order to create the desired final composition. After this nearly completed cream composition has cooled to under preferably about 105° F., first and second sets of nanoparticles which have preferably been manufactured into a natural-based polyphenol can then be added to complete the final cream composition.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLES

Example 1

Several samples of spherical-shaped silver nanoparticle were subjected to dynamic light scattering (DLS) to measure size distribution. Testing was done using a Malvern Nano Zetasizer. Table 1 illustrates the results, showing narrow size distributions of the particles.

TABLE 1

| Set | Diameter (nm) | Std. Dev. |
|---|---|---|
| 1 | 3.097 | 0.8359 |
| 2 | 2.101 | 0.5529 |
| 3 | 4.294 | 0.8361 |
| 4 | 5.782 | 1.541 |
| 5 | 3.701 | 1.028 |
| 6 | 7.187 | 1.861 |
| 7 | 6.713 | 1.853 |
| 8 | 2.105 | 0.5779 |
| 9 | 3.328 | 0.8970 |
| 10 | 8.186 | 1.735 |
| 11 | 5.201 | 1.003 |
| 12 | 7.060 | 1.843 |
| 13 | 6.957 | 1.897 |

Example 2

A nanoparticle composition is prepared and includes a 50% water 50% dimethyl sulfoxide solution having (i) 0.5 ppm spherical Au nanoparticles with a mean diameter of 10 nm with 99% of these Au nanoparticles having a diameter within ±1 nm of that mean diameter, and (ii) 1 ppm of spherical Ag nanoparticles with a mean diameter of 8 nm with 99% of these Ag nanoparticles having a diameter within ±1 nm of that mean diameter. This nanoparticle composition is readily applied to a nail and/or surrounding tissue containing a fungal infection or at risk of developing a fungal infection.

Example 3

A nanoparticle composition is prepared and includes a 40% water 60% dimethyl sulfoxide solution having (i) 1 ppm coral shaped Au nanoparticles with a mean length of 40 nm with 99% of these Au nanoparticles having a cross section within ±6 nm of that mean length, and (ii) 2 ppm of spherical Ag nanoparticles with a mean diameter of 10 nm with 99% of these Ag nanoparticles having a diameter within ±1 nm of that mean diameter. This nanoparticle composition is readily applied to a nail and/or surrounding tissue containing a fungal infection or at risk of developing a fungal infection.

Example 4

A nanoparticle composition is prepared and includes a 30% water 70% dimethyl sulfoxide solution having (i) 3 ppm coral shaped Au nanoparticles with a mean length of 80 nm with 99% of these Au nanoparticles having a cross section within ±10 nm of that mean length, and (ii) 5 ppm of spherical Ag nanoparticles with a mean diameter of 15 nm with 99% of these Ag nanoparticles having a diameter within ±1.5 nm of that mean diameter. This nanoparticle composition is readily applied to a nail and/or surrounding tissue containing a fungal infection or at risk of developing a fungal infection.

Example 5

A nanoparticle composition is prepared and includes a 10% water 90% dimethyl sulfoxide solution having (i) 3 ppm coral shaped Au nanoparticles with a mean length of 80 nm with 99% of these Au nanoparticles having a cross section within ±10 nm of that mean length, and (ii) 5 ppm of spherical Ag nanoparticles with a mean diameter of 15 nm with 99% of these Ag nanoparticles having a diameter within ±1.5 nm of that mean diameter. This nanoparticle composition is readily applied to a nail and/or surrounding tissue containing a fungal infection or at risk of developing a fungal infection.

Example 6

A cream based carrier suitable for carrying a multicomponent antimicrobial composition is prepared by heating stearic acid, olive oil, and emulsifying wax to between 160 and 200° F. Nanoparticles and an amount of dimethyl sulfoxide are suitably added after cooling the composition to about 105° F. or less.

Example 7

A nanoparticle composition is prepared by adding to the cream carrier of Example 6 (i) 3 ppm coral shaped Au nanoparticles with a mean length of 80 nm with 99% of these Au nanoparticles having a cross section within ±10 nm of that mean length, and (ii) 5 ppm of spherical Ag nanoparticles with a mean diameter of 15 nm with 99% of these Ag nanoparticles having a diameter within ±1.5 nm of that mean diameter. This nanoparticle composition is readily applied to a nail and/or surrounding tissue containing a fungal infection or at risk of developing a fungal infection.

Example 8

A nanoparticle composition is prepared by adding to the cream carrier of Example 6 (i) 3 ppm coral shaped Au nanoparticles with a mean length of 80 nm with 99% of these Au nanoparticles having a cross section within ±10 nm of that mean length, and (ii) 5 ppm of spherical Ag nanoparticles with a mean diameter of 15 nm with 99% of these Ag nanoparticles having a diameter within ±1.5 nm of that mean diameter. This nanoparticle composition is readily applied to a nail and/or surrounding tissue containing a fungal infection or at risk of developing a fungal infection.

Example 9

A nanoparticle composition is prepared by mixing the nanoparticle composition of Example 5 with a gelling agent in an amount sufficient to form a gel. The resulting gel is readily applied to a nail and/or surrounding tissue containing a fungal infection or at risk of developing a fungal infection.

Example 10

A nanoparticle composition is prepared by mixing the nanoparticle composition of Example 5 with a petroleum jelly carrier. The resulting composition is readily applied to a nail and/or surrounding tissue containing a fungal infection or at risk of developing a fungal infection.

Example 11

A nanoparticle composition is prepared by mixing the nanoparticle composition of Example 5 with a cornstarch powder and subjecting the mixture to desiccation. The resulting dry powder is readily applied to a nail and/or surrounding tissue containing a fungal infection or at risk of developing a fungal infection.

The invention claimed is:

1. A nanoparticle composition for treating or preventing onychomycosis, the composition comprising:
a first plurality of ground-state, nonionic silver nanoparticles formed through a laser ablation process, the silver nanoparticles having no external edges or bond angles, and having a mean diameter and a particle size distribution such that 99% of the silver nanoparticles have a diameter within ±3 nm of the mean diameter, the silver nanoparticles providing an antifungal effect without release of silver ions and having reduced toxicity as compared to silver ions; and
a penetrating solvent selected from the group consisting of dimethyl sulfoxide (DMSO), alcohols, ketones, esters, fatty acids, diols, amines, surfactants, and alkanes, and that is configured to penetrate a targeted treatment area of a nail and/or surrounding tissue,
wherein the silver nanoparticles are included in the composition at a concentration of about 0.5 ppm to about 100 ppm.

2. The nanoparticle composition of claim 1, wherein the penetrating solvent comprises DMSO and water.

3. The nanoparticle composition of claim 1, wherein the first plurality of silver nanoparticles are included at a concentration of about 1 to 15 ppm.

4. The nanoparticle composition of claim 1, wherein the first plurality of silver nanoparticles are spherical-shaped.

5. The nanoparticle composition of claim 4, wherein the spherical-shaped silver nanoparticles have a mean diameter of about 9 nm to about 20 nm.

6. The nanoparticle composition of claim 4, wherein the spherical-shaped silver nanoparticles have a mean diameter of about 12 nm to about 15 nm.

7. The nanoparticle composition of claim 4, further comprising a second plurality of metal nanoparticles, the second plurality of metal nanoparticles being coral-shaped, each coral-shaped metal nanoparticle having a non-uniform cross section and a globular structure of multiple, non-linear strands joined together without right angles.

8. The nanoparticle composition of claim 7, wherein the coral-shaped nanoparticles have a mean particle size of about 40 nm to about 100 nm.

9. The nanoparticle composition of claim 7, wherein the coral-shaped nanoparticles are present at a concentration of between about 1 and about 10 ppm.

10. The nanoparticle composition of claim 1, wherein at least 99% of the first plurality of silver nanoparticles have a diameter within ±1 nm of the mean diameter.

11. The nanoparticle composition of claim 1, wherein the first plurality of metal nanoparticles have an absolute value ξ-potential of at least 10 mV.

12. The nanoparticle composition of claim 1, wherein the first plurality of metal nanoparticles have an absolute value ξ-potential of at least 30 mV.

13. A nanoparticle composition for treating or preventing onychomycosis, the composition comprising:
a plurality of spherical-shaped metal nanoparticles;
a plurality of coral-shaped metal nanoparticles having a non-uniform cross section and a globular structure of multiple, non-linear strands joined together without right angles; and
a penetrating solvent configured to penetrate a targeted treatment area of a nail and/or surrounding tissue,
wherein the spherical-shaped metal nanoparticles and/or the coral-shaped metal nanoparticles provide an antifungal effect without release of metal ions.

14. The nanoparticle composition of claim 13, wherein the spherical-shaped metal nanoparticles have a mean diameter of about 9 nm to about 20 nm.

15. The nanoparticle composition of claim 13, wherein the spherical-shaped metal nanoparticles have a particle size distribution such that 99% of the metal nanoparticles have a diameter within ±3 nm of the mean diameter.

16. The nanoparticle composition of claim 13, wherein the coral-shaped metal nanoparticles have a mean length of about 40 nm to about 100 nm.

17. A nanoparticle composition for treating or preventing onychomycosis, the composition comprising:
a first plurality of metal nanoparticles comprised of silver, gold, or alloy thereof and that are formed through a laser ablation process, the metal nanoparticles having no external edges or bond angles, and having a mean particle size within a range of about 5 nm to about 40 nm and having a particle size distribution such that 99% of the metal nanoparticles have a diameter within ±3 nm of the mean particle size, the metal nanoparticles providing an antifungal effect without release of metal ions;
a second plurality of metal nanoparticles that differ from the first plurality of metal nanoparticle by mean particle size and at least one of particle shape or type of metal, the mean particle size of the second plurality of metal nanoparticles being larger than the mean particle size of the first plurality of metal nanoparticles; and
a penetrating solvent configured to penetrate a targeted treatment area of a nail and/or surrounding tissue.

18. The nanoparticle composition of claim 17, wherein the first plurality of metal nanoparticles are silver and wherein the second plurality of metal nanoparticles are gold.

19. A nanoparticle composition for treating or preventing onychomycosis, the composition comprising:
a plurality of ground state, nonionic metal nanoparticles comprised of a gold-silver alloy and that are formed through a laser ablation process, the ground state, nonionic metal nanoparticles having no external edges or bond angles and providing an antifungal effect without release of metal ions; and an aqueous penetrating comprised of dimethyl sulfoxide (DMSO) and water and configured to penetrate a targeted treatment area of a nail and/or surrounding tissue.

20. A nanoparticle composition for treating or preventing onychomycosis, the composition comprising:
a first plurality of ground-state, nonionic silver nanoparticles formed through a laser ablation process, the metal nanoparticles having no external edges or bond angles, and having a mean diameter and a particle size distribution such that 99% of the silver nanoparticles have a diameter within ±3 nm of the mean diameter, the silver nanoparticles providing an antifungal effect without release of silver ions and having reduced toxicity as compared to silver ions; and
a penetrating solvent configured to penetrate a targeted treatment area of a nail and/or surrounding tissue,
wherein the silver nanoparticles are included in the composition at a concentration of about 0.5 ppm to about 100 ppm.

* * * * *

UNITED STATES PATENT AND TRADEMARK OFFICE
CERTIFICATE OF CORRECTION

PATENT NO.         : 10,201,571 B2
APPLICATION NO.    : 15/415562
DATED              : February 12, 2019
INVENTOR(S)        : William H. Niedermeyer It is certified that error appears in the above-identified patent and that said Letters Patent is hereby corrected as shown below:

On the Title Page

Item (54) and in the Specification, Column 1, Line 3, Title, change "Onychomychosis" to –Onychomycosis–

Page 2
Item (56), References Cited, U.S. Patent Documents, add "20100272770 10/2010 De Windt, et al."

Page 3
Item (56), References Cited, Other Publications, change "Santos et al; "Enhancemetn of antibiotic effect via gold:silver-alloy nanoparticles", J. Nanopart Res (2012) 14:859, pp. 1-8." to –Santos et al; "Enhancement of antibiotic effect via gold:silver-alloy nanoparticles", J. Nanopart Res (2012) 14:859, pp. 1-8.–

In the Specification

Column 3
Line 8, change "resistance" to –resistant–

Column 6
Line 34, change second instance of "and" to –a–

Column 8
Line 5, change "agent, For" to –agent. For–
Line 32, change "as stabilizing" to –as the stabilizing–
Lines 36-37, change "as stabilizing" to –as the stabilizing–

Column 10
Line 27, change "may an" to –may have an–

Signed and Sealed this
Third Day of September, 2019

Andrei Iancu
*Director of the United States Patent and Trademark Office*

In the Claims

Column 15
Line 1, after "penetrating" insert --solvent--